(12) United States Patent
   Purcell

(10) Patent No.: US 10,932,822 B2
(45) Date of Patent: Mar. 2, 2021

(54) MULTI-AXIAL OCCIPITAL PLATE

(71) Applicant: Astura Medical Inc., Carlsbad, CA (US)

(72) Inventor: Thomas Purcell, Carlsbad, CA (US)

(73) Assignee: Astura Medical Inc, Carlsbad, CA (US)

( * ) Notice: Subject to any disclaimer, the term of this patent is extended or adjusted under 35 U.S.C. 154(b) by 187 days.

(21) Appl. No.: 16/167,420

(22) Filed: Oct. 22, 2018

(65) Prior Publication Data

US 2019/0117274 A1  Apr. 25, 2019

Related U.S. Application Data

(60) Provisional application No. 62/575,467, filed on Oct. 22, 2017.

(51) Int. Cl.
*A61B 17/70* (2006.01)
*A61B 17/80* (2006.01)

(52) U.S. Cl.
CPC ...... *A61B 17/7055* (2013.01); *A61B 17/7044* (2013.01); *A61B 17/8061* (2013.01)

(58) Field of Classification Search
CPC ............ A61B 17/7055; A61B 17/7044; A61B 17/8061
See application file for complete search history.

(56) References Cited

U.S. PATENT DOCUMENTS

| 7,695,500 | B2 | 4/2010 | Markworth |
| 8,986,351 | B2 * | 3/2015 | Gephart ................. A61B 17/70 606/246 |
| 9,232,966 | B2 | 1/2016 | Refai |
| 2011/0190824 | A1 | 8/2011 | Gephart |
| 2017/0290608 | A1 * | 10/2017 | Neal ................. A61B 17/7052 |

FOREIGN PATENT DOCUMENTS

CN        200998297 Y      1/2008

OTHER PUBLICATIONS

International Search Report and Written Opinion in PCT Application No. PCT/US2018/056949 dated Dec. 26, 2018.

* cited by examiner

*Primary Examiner* — Kevin T Truong
*Assistant Examiner* — Tracy L Kamikawa
(74) *Attorney, Agent, or Firm* — Michael R Shevlin

(57) ABSTRACT

Embodiments of the present invention are directed to an occipital plate for fixating the occipital/cervical junction between cranium and the spine configured to provide multi-axial adjustment for the rod connectors including Anterior/Posterior movement, Medial/Lateral movement and Converging/Diverging movement. Some embodiments of the present invention use a variety of components to achieve a range of motion in several different axes. This extended range of motion allows the plate to adapt to the surrounding anatomy as well as making it more facile to adapt to a posterior rod fixation system.

14 Claims, 3 Drawing Sheets

MULTI-AXIAL OCCIPITAL PLATE

CROSS-REFERENCE TO RELATED APPLICATIONS

This application claims the benefit of U.S. Provisional Application No. 62/575,467, filed Oct. 22, 2017, which is incorporated herein by reference.

FIELD

The present invention relates generally to the field of surgery, and more specifically, to a multi-axial occipital plate which may be used in conjunction with a posterior rod system to fixate the occipital/cervical junction between the cranium and the spine.

BACKGROUND

Occipito-cervical fixation has been achieved using a variety of techniques which generally provide stabilization of the base of the skull with respect to the neck. Standard occipital plates do not have enough adjustment to accommodate the varying anatomy and variability in the connecting rods from the cervical spine. Current devices cannot maintain their position once adjusted and "flop around" during the installation process.

It would be desirable to have an occipital plate with multiple adjustment options, such as Anterior/Posterior, Medial/Lateral and Converging/Diverging. It is with this need in mind that the present invention was developed.

SUMMARY OF THE INVENTION

Embodiments of the present invention are directed to an occipital plate for fixating the occipital/cervical junction between cranium and the spine configured to provide multi-axial adjustment for the rod connectors including Anterior/Posterior movement, Medial/Lateral movement and Converging/Diverging movement. Some embodiments of the present invention use a variety of components to achieve a range of motion in several different axes. This extended range of motion allows the plate to adapt to the surrounding anatomy as well as making it more facile to adapt to a posterior rod fixation system.

In one embodiment, a multi-axial occipital plate is presented which includes a fixation plate having one or more double swivel connections, at least one rod connector configured to be coupled to the double swivel connections of the multi-axial fixation plate, and at least one posterior cervical rod configured to be coupled to the at least one rod connector.

In another embodiment, a multi-axial occipital plate is presented which includes a fixation plate having two double swivel connections, two rod connectors configured to be coupled to the double swivel connections, and two posterior cervical rods, each configured to be coupled to each of the two rod connectors.

In some embodiments, the components of the adjustable occipital plate may be initially variable and free to move, but may also be locked in a static position once correct placement is achieved in a patient.

Further embodiments, features, objects and advantages of the invention, as well as structure and operation of various embodiments of the invention, are disclosed in detail below with references to the accompanying drawings. There has thus been outlined, rather broadly, the more important features of the invention in order that the detailed description thereof may be better understood, and in order that the present contribution to the art may be better appreciated. There are additional features of the invention that will be described hereinafter and which will form the subject matter of the claims appended hereto. The features listed herein and other features, aspects and advantages of the present invention will become better understood with reference to the following description and appended claims.

BRIEF DESCRIPTION OF THE DRAWINGS

The present embodiments may be understood from the following detailed description when read in conjunction with the accompanying figures. It is emphasized that the various features of the figures are not necessarily to scale. On the contrary, the dimensions of the various features may be arbitrarily expanded or reduced for clarity.

DETAILED DESCRIPTION

Embodiments of the invention will now be described with reference to the figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein.

Broadly, the present invention provides a multi-axial occipital plate that is used to attach midline of the occiput using occipital screws and then connects to the cervical spine using cervical rods to provide stabilization to the occipito-cervical junction. The multi-axial occipital plate may be supplied as a pre-assembled device having 6 unique components; plate, rod connector with rod connector splines, bottom splines, top splines, springs and plate setscrews. These unique components allow multiple adjustment options for the multi-axial occipital plate, including Anterior/Posterior, Medial/Lateral and Converging/Diverging.

Figure 1:
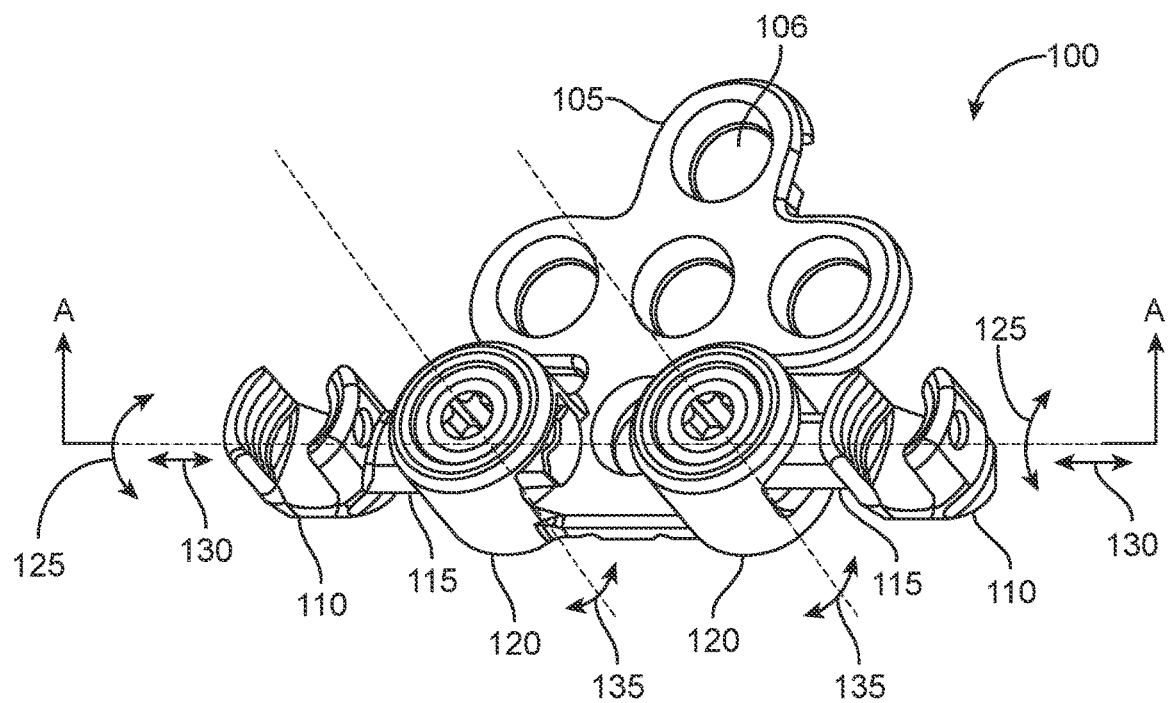
FIG. 1 is a perspective view showing one embodiment of a multi-axial occipital plate system.

FIG. 1 shows one embodiment of multi-axial occipital plate system 100 having a plate 105 and rod connectors 110 with rod connector splines 115, the rod connector arms 115 being couple to the plate via double swivel receivers 120 configured to provide multi-axial adjustment for the rod connectors 110 including Anterior/Posterior movement 125, Medial/Lateral movement 130 and Converging/Diverging movement 135. The plate 105 includes multiple openings 106 configured to accommodate attachment screws, such as cervical screws or any other type of bone screws or attachment/fastening means/devices.

Figure 2:
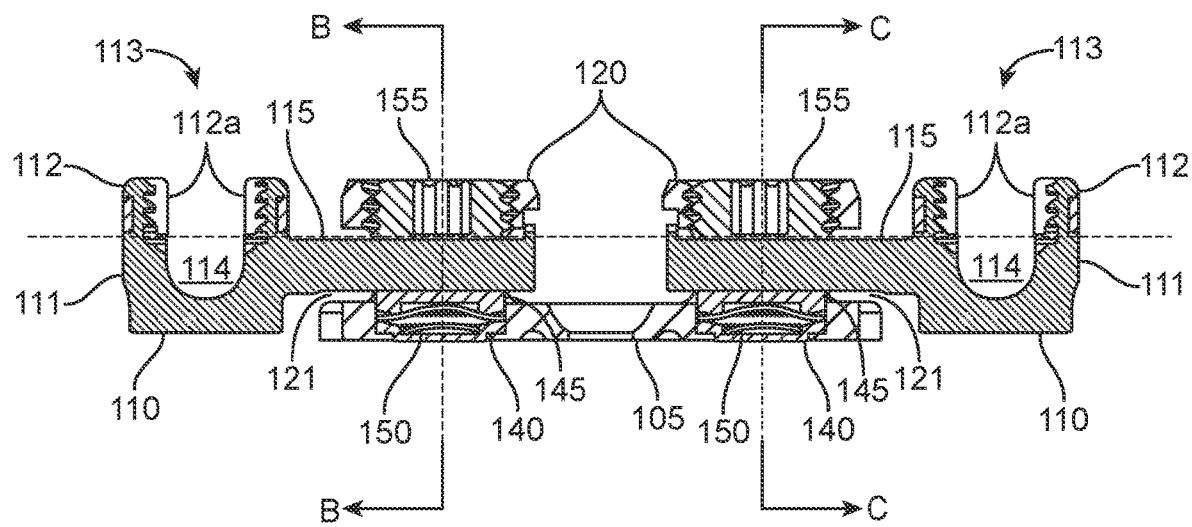
FIG. 2 is a cross-sectional view at A-A of FIG. 1.

FIG. 2 is a cross-sectional view at A-A of FIG. 1 showing more details of the multi-axial occipital plate system 100 including the plate 105, rod connectors 110 and rod connector splines 115 coupled with the double swivel receivers 120. Inside the double swivel receivers 120 are bottom splines 140 and top splines 145 separated by springs 150, and spring and plate setscrews 155 that holds everything in place. The bottom splines 140 include a plurality of grooves on an upper surface 141 configured to rotationally engage a plurality of grooves on a lower surface 146 of the top splines 145. In addition, the top splines 145 include plurality of grooves on an upper surface 147 configured to rotational engage a plurality of grooves along a lower surface 116 of the rod connector splines 115. This design has a friction fit mechanism which ensures the components do no move from their desired location which allows for easier attachment of components.

The double swivel receiver 120 includes a tunnel opening 121 in the walls sized to receive the rod connector spline 115 between the top spline 145 and plate setscrew 155. The tunnel opening 121 can extend through the double swivel receiver 120 so that the rod connector spline 115 can extend beyond the double swivel receiver 120 and allow multi-axial movement of the rod connectors 110 in relation to the plate 105.

Figure 3:
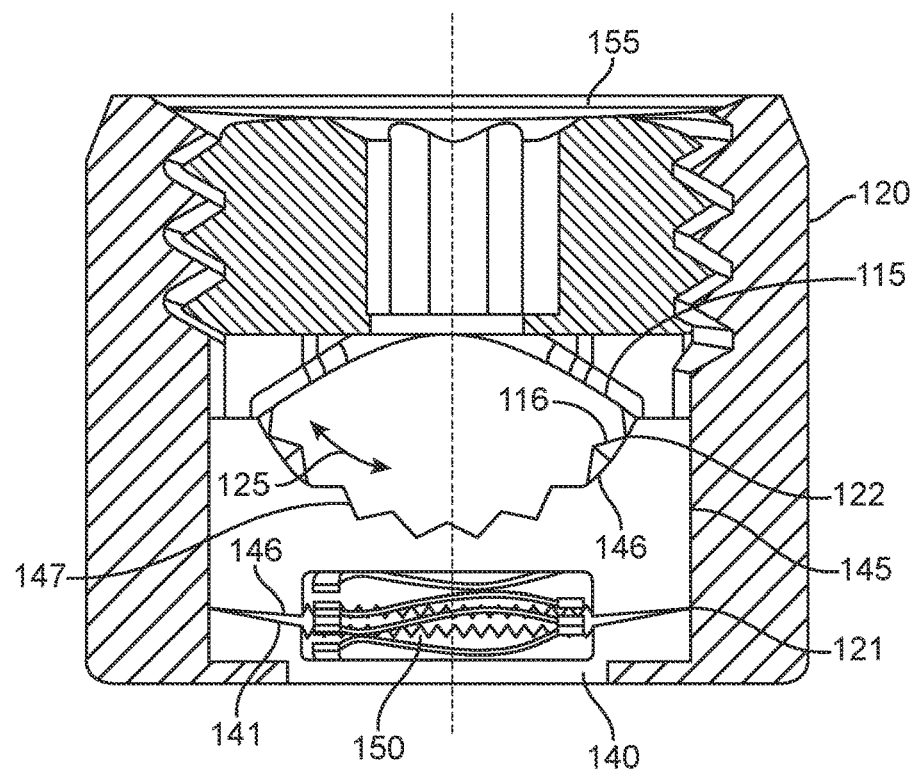
FIG. 3 is a cross-sectional view at B-B of FIG. 2.
Figure 4:
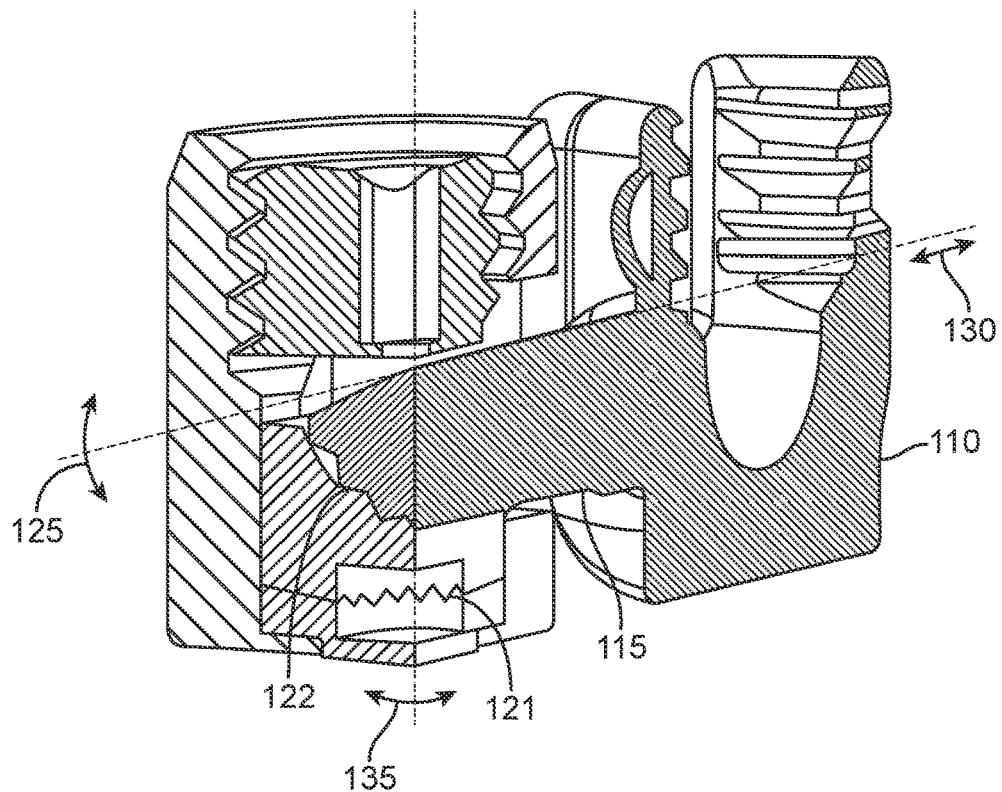
FIG. 4 is a perspective cross-sectional view at C-C of FIG. 2.

FIG. 3 is a cross-sectional view at B-B of FIG. 2 and FIG. 4 is a perspective cross-sectional view at C-C of FIG. 2 showing multi-axial adjustment between the components. The primary mechanism which differentiates this device is the "double swivel" between the components. This "double swivel" is located within the double swivel receiver 120 and comprises a lower swivel 121 and an upper swivel 122. The lower swivel 121 is a rotational motion around a first axis 170 between the bottom splines 140 and top splines 145 providing Converging/Diverging movement 135 for the rod connectors 110. The upper swivel 122 is a rotational motion around a second axis 175 between top splines 145 and rod connector splines 115 providing Anterior/Posterior movement 125 for the rod connectors 110. In addition to the "double swivel", the rod connector spline 115 may be slid side-to-side in relation to the top splines 145 providing Medial/Lateral movement 130 for the rod connectors 110. The spring 150 provides a friction fit between the components while the adjustments are made. The plate setscrew 155 may be tightened to statically secure the bottom splines 140, top splines 145 and the rod connector spline 115 in position. The multi-axial adjustment feature allows a surgeon to custom-fit the occipital plate to a patient in accordance with patient's physiological characteristics and needs.

Figure 5:
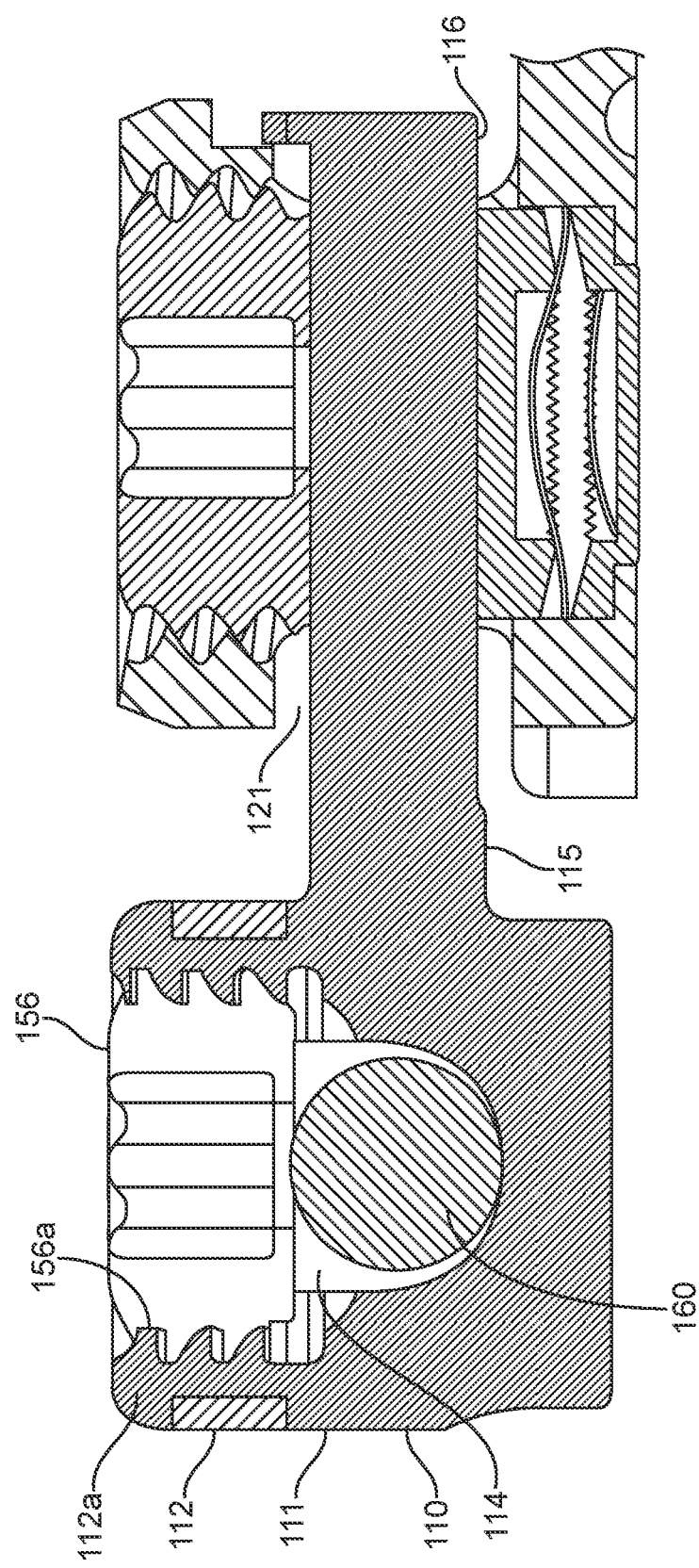
FIG. 5 is a partial cross-sectional view at A-A of FIG. 1.

FIG. 5 is a partial cross-sectional view at A-A of FIG. 1 showing a cervical rod 160 positioned within the rod connector 110. In the embodiment shown, the rod connector 110 comprises a body member 111 and lateral connector 115 extending integrally from the body member 111, as illustrated in the figures. In one embodiment, the body member 111 includes a side wall 112 that defines a central opening 113 in the body member 111. The body member 111 may further include a threaded portion 112a on the side walls 112. A channel 114 is defined by a pair of apertures or ended slots are oppositely disposed through the side wall 112. The slots 114 include an open end 114a sized to allow a fixation rod to be loaded into the slots 114 from the open end 114a. A rod connector setscrew 156 includes a threaded edge 156a configured to interact with the threaded portion 112a when the rod connector setscrew 156 is inserted into the channel 114 to secure the cervical rod 160.

To secure the cervical rod 160 to the rod connector 110, the cervical rod 160 is placed inside the channel 114 and the rod connector setscrew 156 is tightened securing the cervical rod 160 to the rod connector 110.

As discussed above, the multi-axial occipital plate system 100 is configured for multi-axial translations and rotations to allow a surgeon to custom-fit the occipital plate to a patient in accordance with patient's physiological characteristics and needs.

During use, the rod connector setscrew 156 is loosened to allow the rod connector 110 to translate (medial lateral 130) and rotate (anterior/posterior 135). When in the loosened state, the spring 150 maintains friction between the components, so that the rod connector 110 stay in the desired position. A cervical rod 160 spanning from the cervical construct is placed into the rod connector slot 114 and torqued in place with the rod connector setscrew 156.

Once the cervical rod 160 is attached, the plate setscrew 155 is torqued which engages the bottom spline 140, top spline 145, and rod connector spline 115 to eliminate translation (medial lateral 130) and rotation (anterior posterior 135).

To use the multi-axial occipital plate system 100, the surgeon examines the patient to determine patient's physical characteristics and based on those characteristics selects an appropriate multi-axial occipital plate system 100. The surgeon may make initial adjusts of the rod connector 110 by translating/rotating them for the proper orientation (i.e., multi-axial adjustment).

The surgeon may then insert the cervical rods into the channels of the rod connectors and once the rods are set to a specific position, they may be secured by tightening the setscrews using a tightening tool (such as a wrench, a screwdriver, allen-wrench, and the like). The surgeon may then finalize any adjustment and secure the rod connector 104 to the plate by tightening the plate screws 124 using a tightening tool.

The multi-axial adjustment of the multi-axial occipital plate system 100 may be performed when the fixation plate 105 is coupled to the patient's spine. Thus, a surgeon can install the multi-axial occipital plate system 100 into the patient' spine and then rotate and translate various components and, after that, lock them into a static configuration. Thus, prior to installation, the multi-axial occipital plate system 100 may have a variety of motions about its various axes, but once it is installed, it may be secured in a static non-moving position. Alternatively, the mufti-axial occipital plate system 100 may be adjusted outside of the patient's body, then locked into a static configuration. In another alternate embodiment, the multi-axial occipital plate system 100 may be partially adjusted and secured outside of the patient's body, then installed to the patient spine, and finalized adjustment made inside the body then locked into a static configuration.

While embodiments and applications of this invention have been shown and described, it would be apparent to those skilled in the art that many more modifications than mentioned above are possible without departing from the inventive concepts herein.

The invention claimed is:

1. A multi-axial occipital plate system comprising:
   an occipital plate having first and second double swivel receivers; the first double swivel receiver having a first upper swivel and a first lower swivel located within the first double swivel receiver, and the second double swivel receiver having a second upper swivel and a second lower swivel located within the second double swivel receiver;
   wherein each double swivel receiver includes a bottom spline, a top spline, and a spring;
   a first rod connector having a first rod connector arm coupled to the first double swivel receiver;

a second rod connector having a second rod connector arm coupled to the second double swivel receiver; and
a first plate set screw being configured to secure the first rod connector arm in the first double swivel receiver and a second plate set screw being configured to secure the second rod connector arm in the second double swivel receiver;
wherein the first and second double swivel receivers are configured to provide multi-axial movement between the respective one of the first and second rod connectors and the occipital plate:
wherein the multi-axial movement includes:
converging/diverging movement for the rod connector from rotational motion of the lower swivel around a first axis;
anterior/posterior movement for the rod connector from rotational motion of the upper swivel around a second axis; and
medial/lateral movement for the rod connector from a side-to-side sliding relationship with the double swivel receiver;
wherein the rotational motion of each lower swivel is between
the bottom spline having a plurality of grooves on an upper surface; and
a top spline having a plurality of grooves on a lower surface, wherein the plurality of grooves on the upper surface of the bottom spline are configured to rotationally engage the plurality of grooves on the lower surface of the top spline resulting in the converging/diverging movement; and
the rotational motion of each upper swivel is between
the top spline further including a plurality of grooves on an upper surface; and
the respective rod connector arm having a plurality of grooves along a lower surface, wherein the plurality of grooves on the upper surface of the top spline are configured to rotationally engage the plurality of grooves along the lower surface of the respective rod connector arm resulting in the anterior/posterior movement; wherein each spring separates the respective top and bottom splines and is configured to provide a frictional fit between the bottom spline, the top spline, and the rod connector arm while adjustments are made.

2. The system of claim 1, wherein the movement of first rod connector is independent of the movement of the second rod connector.

3. The system of claim 1, wherein each double swivel receiver includes a tunnel opening in its walls sized to receive the respective rod connector arm between the top spline and the plate set screw.

4. The system of claim 1, wherein each of the first and second rod connectors includes a body member having a channel configured to receive a cervical rod and a rod connector set screw configured to couple with the body member and secure the cervical rod in the channel.

5. A multi-axial occipital plate system comprising:
an occipital plate having first and second double swivel receivers, each double swivel receiver having:
a bottom spline having a plurality of grooves on an upper surface;
a top spline having a plurality of grooves on an upper surface and a lower surface, wherein the plurality of grooves on the upper surface of the bottom spline are configured to rotationally engage the plurality of grooves on the lower surface of the top spline;
a spring separating the top and bottom splines configured to provide a frictional fit between the bottom spline and the top spline; and
a plate set screw coupled to the top and bottom splines;
and first and second rod connectors coupled to a respective one of the first and second double swivel receivers, each rod connector having:
a rod connector arm with a plurality of grooves along a lower surface coupled to the plurality of grooves on the upper surface of the respective top spline;
the rod connector arm being in a side-to-side sliding relationship with the respective double swivel receiver; and
the plate set screw being configured to secure the rod connector arm in the respective double swivel receiver;
wherein the first and second double swivel receivers are configured to provide multi-axial movement between the respective one of the first and second rod connectors and the occipital plate.

6. The system of claim 5, wherein the multi-axial movement includes anterior/posterior movement, medial/lateral movement and converging/diverging movement between the respective one of the first and second rod connectors and the occipital plate.

7. The system of claim 5, wherein the movement of the first rod connector is independent of the movement of the second rod connector.

8. The system of claim 5, wherein each double swivel receiver includes a lower swivel comprising the rotational engagement between the bottom spline and the top spline configured for rotational motion of the rod connector around a first axis and an upper swivel comprising rotational engagement between the top spline and the respective rod connector arm configured for rotational motion of the rod connector around a second axis.

9. The system of claim 8, wherein the rotational motion around the first axis results in converging/diverging movement of the rod connector and the rotational motion around the second axis results in anterior/posterior movement of the rod connector.

10. The system of claim 5, wherein the side-to-side sliding relationship provides medial/lateral movement for the rod connector.

11. The system of claim 5, wherein each double swivel receiver includes a tunnel opening in its walls sized to receive the respective rod connector arm between the top spline and the plate set screw.

12. A multi-axial occipital plate system comprising:
an occipital plate having first and second double swivel receivers;
a first rod connector having a first rod connector arm coupled to the first double swivel receiver in a side-to-side sliding relationship providing medial/lateral movement for the first rod connector; and
a second rod connector having a second rod connector arm coupled to the second double swivel receiver in a side-to-side sliding relationship providing medial/lateral movement for the second rod connector;
wherein the first and second double swivel receivers are configured to provide multi-axial movement between the respective one of the first and second rod connectors and the occipital plate:
wherein each double swivel receiver includes:
a bottom spline having a plurality of grooves on an upper surface;

a top spline having a plurality of grooves on a lower surface, wherein the plurality of grooves on the upper surface of the bottom spline are configured to rotationally engage the plurality of grooves on the lower surface of the top spline;

the top spline further including a plurality of grooves on an upper surface configured to rotationally engage a plurality of grooves along a lower surface of the respective rod connector arm;

a spring separating the top and bottom splines configured to provide a frictional fit between the bottom spline, the top spline, and the rod connector arm while adjustments are made; and a plate set screw coupled to the top and bottom splines being configured to secure the respective rod connector arm in the double swivel receiver.

13. The system of claim 12, wherein each double swivel receiver includes a lower swivel comprising the rotational engagement between the bottom spline and the top spline configured for rotational motion of the rod connector around a first axis resulting in converging/diverging movement of the rod connector and an upper swivel comprising the rotational engagement between the top spline and the respective connector arm configured for rotational motion of the rod connector around a second axis resulting in anterior/posterior movement of the rod connector.

14. The system of claim 12, wherein each double swivel receiver includes a tunnel opening in its walls sized to receive the respective rod connector arm in a side-to-side sliding relationship between the top spline and the plate set screw resulting in medial/lateral movement of the rod connector.

\* \* \* \* \*